(12) United States Patent
Isomura et al.

(10) Patent No.: US 7,927,475 B2
(45) Date of Patent: Apr. 19, 2011

(54) GAS SENSOR

(75) Inventors: Hiroshi Isomura, Aichi (JP); Shoji Akatsuka, Kasugai (JP); Osamu Shinkai, Aichi (JP)

(73) Assignee: NGK Spark Plug Co., Ltd. (JP)

( * ) Notice: Subject to any disclaimer, the term of this patent is extended or adjusted under 35 U.S.C. 154(b) by 1125 days.

(21) Appl. No.: 10/879,212

(22) Filed: Jun. 30, 2004

(65) Prior Publication Data
US 2005/0029101 A1 Feb. 10, 2005

(30) Foreign Application Priority Data

Jun. 30, 2003 (JP) .............................. P. 2003-187822

(51) Int. Cl.
*G01N 27/406* (2006.01)
(52) U.S. Cl. ...................................... 204/428
(58) Field of Classification Search .................... 204/428
See application file for complete search history.

(56) References Cited

U.S. PATENT DOCUMENTS

| | | | |
|---|---|---|---|
| 5,762,771 A * | 6/1998 | Yamada et al. ............... | 204/428 |
| 5,880,353 A | 3/1999 | Graser et al. | |
| 6,015,533 A * | 1/2000 | Young et al. ..................... | 422/83 |
| 6,279,376 B1 * | 8/2001 | Yamada et al. ................ | 73/23.2 |
| 6,342,141 B1 | 1/2002 | Nelson | |
| 6,348,141 B1 | 2/2002 | Kato et al. | |
| 6,548,023 B1 * | 4/2003 | Matsuo et al. .................. | 422/83 |
| 2003/0019280 A1 | 1/2003 | Toguchi et al. | |

FOREIGN PATENT DOCUMENTS

| | | |
|---|---|---|
| EP | 1 236 998 A2 | 9/2002 |
| EP | 1 391 724 A1 | 2/2004 |
| JP | 11-505029 A | 5/1999 |
| JP | 2000-171429 A | 6/2000 |
| JP | 2000-304719 A | 11/2000 |
| JP | 2002-162377 A | 6/2002 |
| JP | 2003-107033 A | 4/2003 |
| JP | 2003-161718 A | 6/2003 |

OTHER PUBLICATIONS

European Search Report dated Oct. 28, 2004.
Japanese Office Action dated May 12, 2009.

* cited by examiner

*Primary Examiner* — Jennifer K Michener
*Assistant Examiner* — Dustin Q Dam
(74) *Attorney, Agent, or Firm* — Sughrue Mion, PLLC

(57) ABSTRACT

A gas sensor comprising: the gas sensor element defined; the cylindrical metal shell defined herein; and the protector defined herein, wherein the protector defined herein has a double structure including the cylindrical inner cover portion and the outer cover portion both defined herein, and a leading end portion positioned on a leading end side of the support face of the metal shell, the outer cylindrical portion and the inner cylindrical portion are arranged to construct an inner gas introducing passage for guiding the object gas introduced from the outer gas introducing apertures, between the outer cylindrical portion and the inner cylindrical portion, across a trailing end of the inner cylindrical portion closer to a leading end side, as viewed in an axial direction, than an inner circumferential side end edge of a joining face joining an inner circumference and an outer circumference of a leading end portion of said metal shell, into a clearance between the inner cover portion and the leading end portion of the gas sensor element.

9 Claims, 4 Drawing Sheets

GAS SENSOR

FIELD OF THE INVENTION

The present invention relates to a gas sensor and, more particularly, to a gas sensor provided with a protector for covering such a portion of a gas sensor element having a bottomed cylindrical shape or a plate shape as will be exposed to an object gas to be measured.

BACKGROUND OF THE INVENTION

A gas sensor such as an oxygen sensor, a NOx sensor or an HC sensor is known in the prior art. This gas sensor is generally provided with a protector for covering and protecting such a leading end portion of a gas sensor element as will be exposed to the object gas such as an exhaust gas. The gas sensor having such protector is disclosed in JP-A-2000-171429, JP-A-2002-162377 and JP-A-2000-304719, for example.

In the gas sensor disclosed in JP-A-2000-171429, an element cover (or a protector) has a double tube structure, in which bottomed cylindrical outer and inner tubes are overlap. Side holes for passing the object gas are individually formed in the side portion of the outer tube and in the side portion of the inner tube. The side holes in the outer tube are arranged on the trailing end side, and the side holes of the inner tube are arranged closer to the leading end side than the side holes of the outer tube. Moreover, bottom holes for passing the object gas are also formed in the bottom portion of the outer tube and in the bottom portion of the inner tube.

In the gas sensor disclosed in JP-A-2002-162377, a protective tube (or a protector) is composed of an outer protective tube and an inner protective tube individually having air vent holes. The air vent hole of the outer protective tube is formed in the side wall of the outer protective tube. The air vent hole of the inner protective tube is formed in a flange portion disposed on the trailing end side of the inner protective tube, and this flange portion is arranged in a through hole of a metal shell. Moreover, air vent holes are also formed in the bottom portions of the outer protective tube and the inner protective tube.

In the gas sensor disclosed in JP-A-2000-304719, a protective cover (or a protector) is provided with an inner protective cover covering the leading end portion of a sensor element, an outer protective cover covering the inner protective cover, and an intermediate protective cover interposed between those covers, thereby to construct a triple structure. An outer gas introducing hole of the outer protective cover is formed in the leading end side of the outer protective cover. An intermediate gas introducing hole of the intermediate protective cover is formed in a flange portion, which is disposed at the back of the cylindrical portion and abuts against the inner wall of the outer protective cover. An inner gas introducing hole of the inner protective cover is interposed, as viewed in the axial direction, between the outer gas introducing hole and the inner gas introducing hole. Moreover, an inner gas discharge port is formed in the bottom portion of the inner protective cover.

SUMMARY OF THE INVENTION

In the gas sensor disclosed in JP-A-2000-171429, the object gas introduced from the outside via the side holes of the outer tube flows toward the leading end between the outer tube and the inner tube, and intrudes into the inner tube through the side walls of the inner tube. The object gas then flows toward the leading end in the inner tube. After this, the object gas is partially discharged through the bottom hole of the inner tube and the bottom hole of the outer tube, and partially flows toward the trailing end in the inner tube so that it is discharged to the outside through the side holes in the inner tube and the side holes in the outer tube.

In the gas sensor having such object gas flow, however, the object gas resides on the trailing end side (i.e., closer to the trailing end side than the side holes of the inner tube) in the inner tube thereby to degrade the responsibility of the sensor. In addition, when the gas sensor is used with its leading end being directed downward, the condensed water having intruded together with the object gas from the side holes of the outer tube flows toward the leading end along the outer wall face of the inner tube, and intrudes into the inner tube through the side holes of the inner tube. Moreover, that condensed water may wet the gas detecting element (or the detecting portion). Especially in the gas sensor of JP-A-2000-171429, the side holes of the inner tube are formed near the detecting portion. Therefore, the condensed water having intruded into the inner tube easily wets the detecting portion. In the gas sensor having a heater, the water may wet the detecting portion when the exhaust gas temperature is low (e.g., 100° C. or less) or the water in the exhaust pipe may be splashed by the gas flow to wet the detecting portion. Then, the detecting element may be cracked by the abrupt heating of the heater. Thus, the gas sensor is inferior in the water resistance.

In the gas sensor disclosed in JP-A-2002-162377, the object gas introduced from the outside through the air vent hole of the outer protective tube flows toward the trailing end between the outer protective tube and the inner protective tube so that it intrudes into the inner protective tube through the air vent hole formed in the flange portion of the inner protective tube. Then, the object gas flows toward the leading end in the inner protective tube. After this, the object gas is discharged to the outside through the air vent holes formed in the bottom portions of the inner protective tube and the outer protective tube.

In the gas sensor of this type, however, the air vent hole of the inner protective tube is arranged in the metal shell. Therefore, the distance from the air vent hole to the detecting portion of the sensor element may be elongated (or the communication passage may be elongated) to lower the responsibility of the sensor. In addition, the gas sensor is designed to arrange the flange portion of the inner protective tube in the through hole of the metal shell. It is, therefore, necessary to enlarge the internal diameter of the leading end portion of the metal shell to some extent. On the other hand, the metal shell is naturally required to have a thickness of some extent from the aspect of strength. Therefore, the gas sensor has a tendency to become diametrically larger.

In the gas sensor disclosed in JP-A-2000-304719 the object gas introduced from the outside through the outer gas introducing holes of the outer protective cover flows toward the trailing end between the outer protective cover and the intermediate protective cover, and intrudes into the inside through the intermediate gas introducing holes formed in the flange portion of the intermediate protective cover. The object gas further flows toward the leading end between the intermediate protective cover and the inner protective cover, and intrudes into the inside through the inner gas introducing holes of the inner protective cover. Moreover, the object gas flows toward the leading end in the inner protective cover. After this, the object gas flows through the inner gas exit formed in the bottom portion of the inner protective cover, and is discharge to the outside through the outer gas introducing holes of the outer protective cover.

In this gas sensor, however, the protective cover has the triple structure composed of the outer protective cover, the intermediate protective cover and the inner protective cover.

Thus, the gas sensor is complicated in structure and has a large number of parts and a large number manufacturing steps. Therefore, the gas sensor has a tendency to raise the cost.

The present invention has been conceived in view of the current situations thus far described, and has an object to provide a gas sensor, which is excellent in responsibility and water resistance and which can be manufactured at a reasonable cost.

According to an aspect of the invention, there is provided a gas sensor comprising: a gas sensor element extending in the axial direction and having gas sensing characteristics at least at its own leading end portion; a cylindrical metal shell enclosing the gas sensor element such that the leading end portion of the gas sensor element protrudes from the its own leading end, and having a support face formed on its inner circumference for supporting the axial direction of the gas sensor element; and a protector fixed on the metal shell and covering the leading end portion of the gas sensor element, wherein the protector has a double structure including a cylindrical inner cover portion covering the leading end portion of the gas sensor element through a clearance and a cylindrical outer cover portion arranged around the inner cover portion, wherein the outer cover portion includes an outer cylindrical portion having outer gas introducing apertures capable of introducing an object gas from the outside into the inside of the outer cover portion, wherein the inner cover portion includes: an inner cylindrical portion enclosing the leading end portion of the gas sensor element; and an inner leading end air vent hole positioned on the leading end side of the inner cylindrical portion, and wherein the leading end portion positioned on the leading end side of the support face of the metal shell, the outer cylindrical portion and the inner cylindrical portion are arranged to construct an inner gas introducing passage for guiding the object gas introduced from the outer gas introducing apertures, between the outer cylindrical portion and the inner cylindrical portion, across the trailing end of the inner cylindrical portion closer to the leading end side, as viewed in the axial direction, than the inner circumferential side end edge of a joining face joining the inner circumference and the outer circumference of a leading end portion of the metal shell, into the clearance between the inner cover portion and the leading end portion of the gas sensor element.

The gas sensor of the invention is provided with the outer gas introducing apertures in the outer cylindrical portion of the outer cover portion. Moreover, the gas sensor is provided with the inner gas introducing passage, which is defined by the leading end portion of the metal shell, the outer cylindrical portion of the outer cover portion and the inner cylindrical portion of the inner cover portion. In addition, the gas sensor is provided with the inner leading end through hole, which is positioned in the leading end direction of the inner cover portion.

With this design, the object gas introduced from the outside through the outer gas introducing apertures of the outer cover portion into inside flows toward the trailing end between the outer cover portion and the inner cover portion, and further intrudes into the inside of the inner cover portion via the inner gas introducing passage. After this, the object gas flows toward the leading end through the clearance between the inner cover portion and the leading end portion of the gas sensor element. After this, the object gas is discharged to the outside through the inner leading end through hole. Therefore, the gas sensor has excellent inflow characteristics of the object gas. In case the gas sensor is used with its leading end being directed downward, on the other hand, the condensed water having intruded together with the object gas into the inside through the outer gas introducing apertures flows not into the inner gas introducing passage arranged closer to the trailing end side than the outer gas introducing apertures but to the leading end side along the outer wall face of the inner cylindrical portion of the inner cover portion. As a result, the condensed water hardly wets the gas sensor element thereby to break the gas sensor element. Therefore, this gas sensor is excellent not only in the responsibility but also the water resistance.

Here in the gas sensor disclosed in JP-A-2002-162377, the distance from the air vent hole of the inner protective tube to the detecting portion of the sensor element may be elongated to lower the responsibility of the sensor. In the gas sensor of the invention, on the contrary, the inner gas introducing passage is disposed closer to the leading end side so that the distance from the inner gas introducing passage to the leading end portion of the gas sensor element can be shortened to improve the responsibility of the sensor.

Moreover, the gas sensor disclosed in JP-A-2002-162377 is designed to arrange the flange portion of the inner protective tube in the through hole of the metal shell, as has been described, so that the gas sensor has a tendency to become large-sized. On the contrary, the gas sensor of the invention has the inner gas introducing passage disposed closer to the leading end side so that it can also be small-sized.

In the gas sensor disclosed in JP-A-2000-304719, on the other hand, the protective cover has the triple structure, as has been described, the structure is complicated to increase the number of parts and the number of manufacturing steps. Therefore, the gas sensor has a tendency to have a higher cost. On the contrary, the gas sensor of the invention has the protector of the double structure so that it can reduce the number of parts and the number of manufacturing steps. Therefore, the gas sensor can be manufactured at a reasonable cost.

In the aforementioned gas sensor, moreover, the inner cylindrical portion and the outer cylindrical portion are desirable arranged such that the side wall of the inner cylindrical portion is disposed at a position to confront the outer gas introducing apertures and such that the inner cylindrical portion and the outer cylindrical portion are either parallel to each other or the closer to each other as they go the farther to the leading end side.

In the gas sensor disclosed in JP-A-2000-304719, for example, the side wall of the inner protective cover does not exist at the position to confront the outer gas introducing hole. Therefore, the object gas introduced from the outer gas introducing hole has a tendency to flow out of another outer gas introducing hole. Thus, the gas sensor cannot be said excellent in the gas replacement in the inner protective cover.

In the invention, on the contrary, the side wall of the inner cylindrical portion exists at the position to confront the outer gas introducing apertures, and the inner cylindrical portion and the outer cylindrical portion are either parallel to each other or come the closer to each other as they go the farther to the leading end side. Therefore, the object gas introduced from the outer gas introducing apertures easily flows toward the trailing end along the outer wall face of the inner cylindrical portion so that it can be quickly fed at a high flow rate to the inner gas introducing passage. Thus, the gas sensor is excellent in the gas replacement.

In any of the gas sensors described above, moreover, when the shortest distance between the leading end portion of the metal shell and the trailing end of the inner cylindrical portion is designated by d and when the shortest distance in the axial direction between the trailing end of the inner cylindrical portion and the trailing side end of the outer gas introducing apertures is designated by D, their ratio d/D is desirably within a range from 0.075 to 0.200.

With this construction, the water resistance to the gas sensor element can be improved while realizing the quick response. The responsibility of the sensor may be degraded, if the d/D is less than 0.075, and the water resistance is degraded if the d/D is more than 0.200. It is preferable to set the d/D at 0.080 or more and 0.180 or less, and it is more preferable to set the d/D at 0.100 or more and 0.150 or less. It is also preferable that the absolute value d is at 0.5 mm or more.

In any of the gas sensors described above, moreover, of an inter-cover space between the inner cylindrical portion of the inner cover portion and the outer cylindrical portion of the outer cover portion, shielding portions may be provided closer to the trailing end side than the outer gas introducing apertures for shielding the inter-cover space intermittently in the circumferential direction.

With these shielding portions, the condensed water having intruded together with the object gas can be more effectively prevented from invading into the inside via the inner gas introducing passage while retaining the fluidity of the object gas introduced from the outer gas introducing apertures (that is, the intrusion preventing effect of the condensed water can be improved). Therefore, it is possible to improve the water resistance of the gas sensor better.

When the shielding portions are formed by molding them integrally with the inner cover portion, they can be easily arranged in the inner space of the cover portion between the outer cylindrical portion and the inner cylindrical portion, thereby to make a contribution to a lower cost.

In the aforementioned sensor, moreover, the ratio of the area of the shielding portions to the open area of the outer gas introducing apertures may be set within a range from 5% to 40%.

By setting the ratio of the area of the shielding portions to the open area of the outer gas introducing apertures within a range from 5% to 40%, the intrusion preventing effect of the condensed water can be sufficiently retained while retaining the fluidity of the object gas sufficiently. This intrusion preventing effect of the condensed water may be degraded, if the ratio is less than 5%, and the fluidity of the object gas may be degraded if the ratio is more than 40%. It is preferable to set the ratio at 7.5% or more and 35% or less.

Here, the area of the shielding portions is calculated as the protected area at the time when the surrounding portions are projected from the leading end side to the trailing end side in the axial direction.

In any of the aforementioned gas sensors, moreover: the outer cover portion may include an outer bottom portion positioned on the leading end side of the outer cylindrical portion and having an outer leading end air vent hole; the inner cover portion may include an inner bottom portion positioned on the leading end side of the inner cylindrical portion and having the inner leading end air vent hole; the outer bottom portion and the inner bottom portion either may contact closely with each other or may be positioned close to each other through a clearance of 0.2 mm or less at least between the surrounding portion of the outer leading end air vent hole and the surrounding portion of the inner leading end air vent hole; and the outer leading end air vent hole and the inner leading end air vent hole may communicate with each other.

According to the invention, the outer bottom portion and the inner bottom portion contact closely with each other, and the outer leading end air vent hole and the inner leading end air vent hole communicate with each other. Alternatively, the outer bottom portion and the inner bottom portion are positioned close to each other through the clearance of 0.2 mm or less at least between the surrounding portion of the outer leading end air vent hole and the surrounding portion of the inner leading end air vent hole, and the outer leading end air vent hole and the inner leading end air vent hole communicate with each other. In short, the clearance between the outer bottom portion and the inner bottom portion is substantially closed. With this construction, the object gas hardly flows through the clearance between the outer bottom portion and the inner bottom portion so that the object gas in the inner cover portion can be efficiently discharged to the outside through the inner leading end air vent hole and the outer leading end air vent hole communicating with each other by the Venturi effect of the object gas flowing in the outside.

In the aforementioned gas sensor, moreover, the surrounding portion of the outer leading end air vent hole of the outer cover portion and the surrounding portion of the inner leading end air vent hole of the inner cover portion may be fixed to each other.

By thus fixing the surrounding portion of the outer leading end air vent hole and the surrounding portion of the inner leading end air vent hole to each other, it is possible to prevent the outer cover portion and the inner cover portion reliably from going out of position with respect to each other.

DETAILED DESCRIPTION OF THE INVENTION

An embodiment of the invention will be described with reference to the accompanying drawings.

Figure 1:
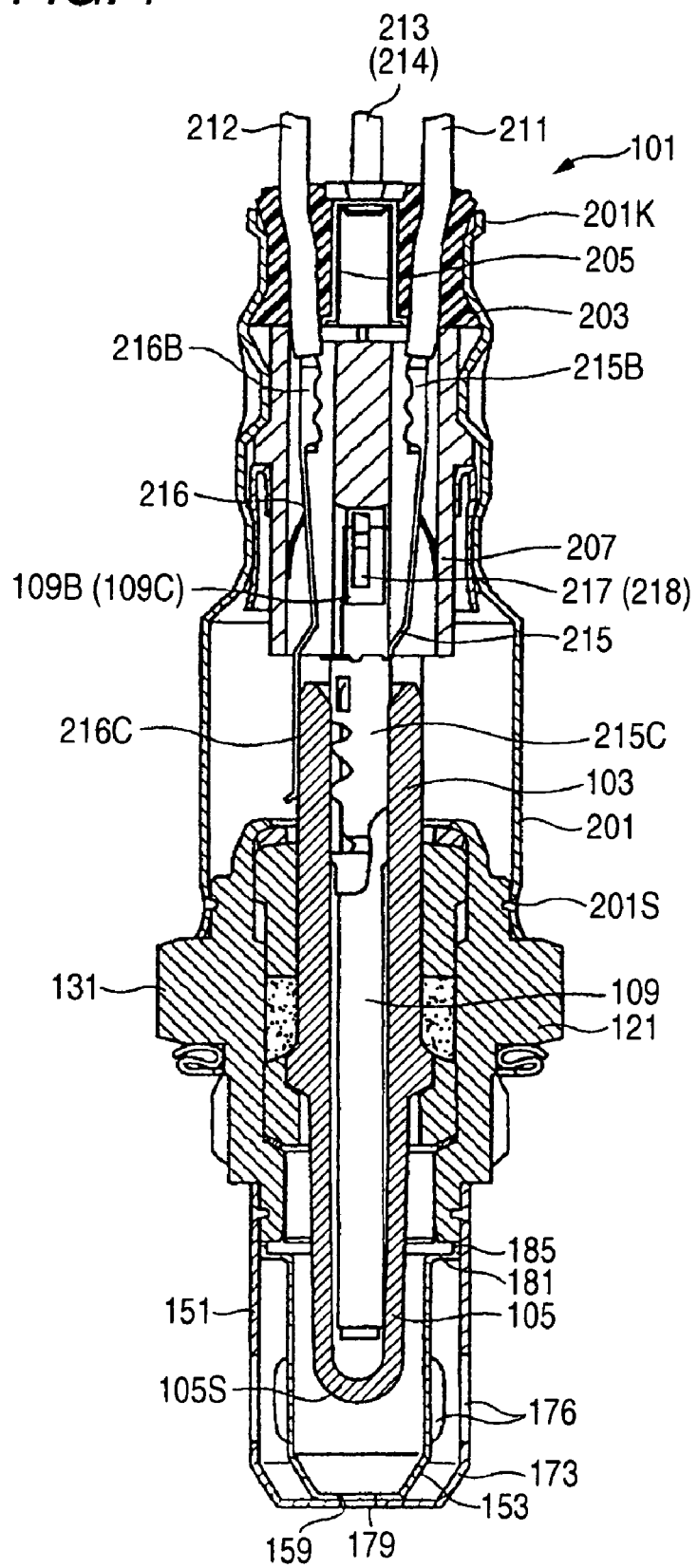
FIG. 1 is a sectional view showing a gas sensor according to an embodiment.
Figure 2:
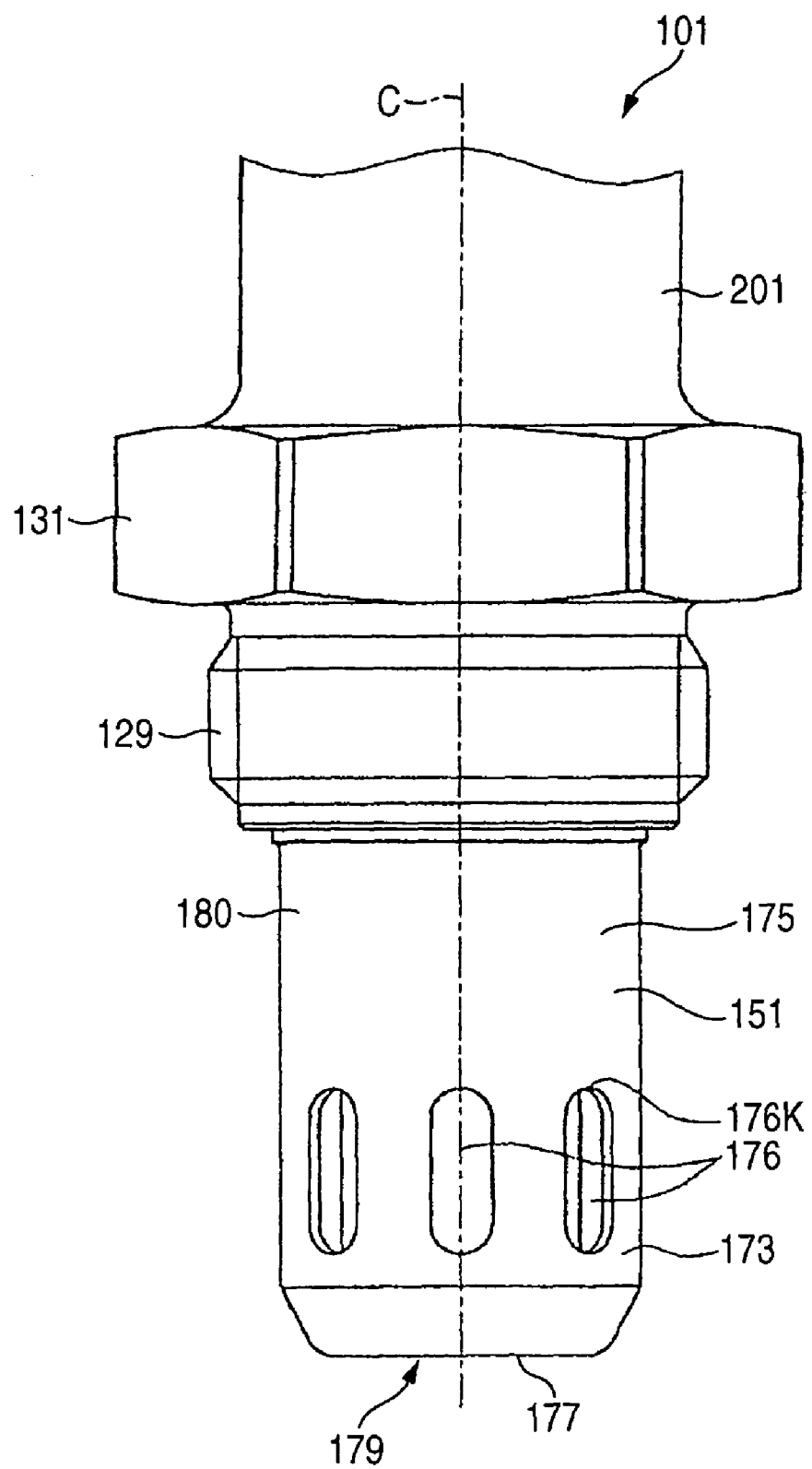
FIG. 2 is a top plan view of an essential portion of the gas sensor according to the embodiment.
Figure 3:
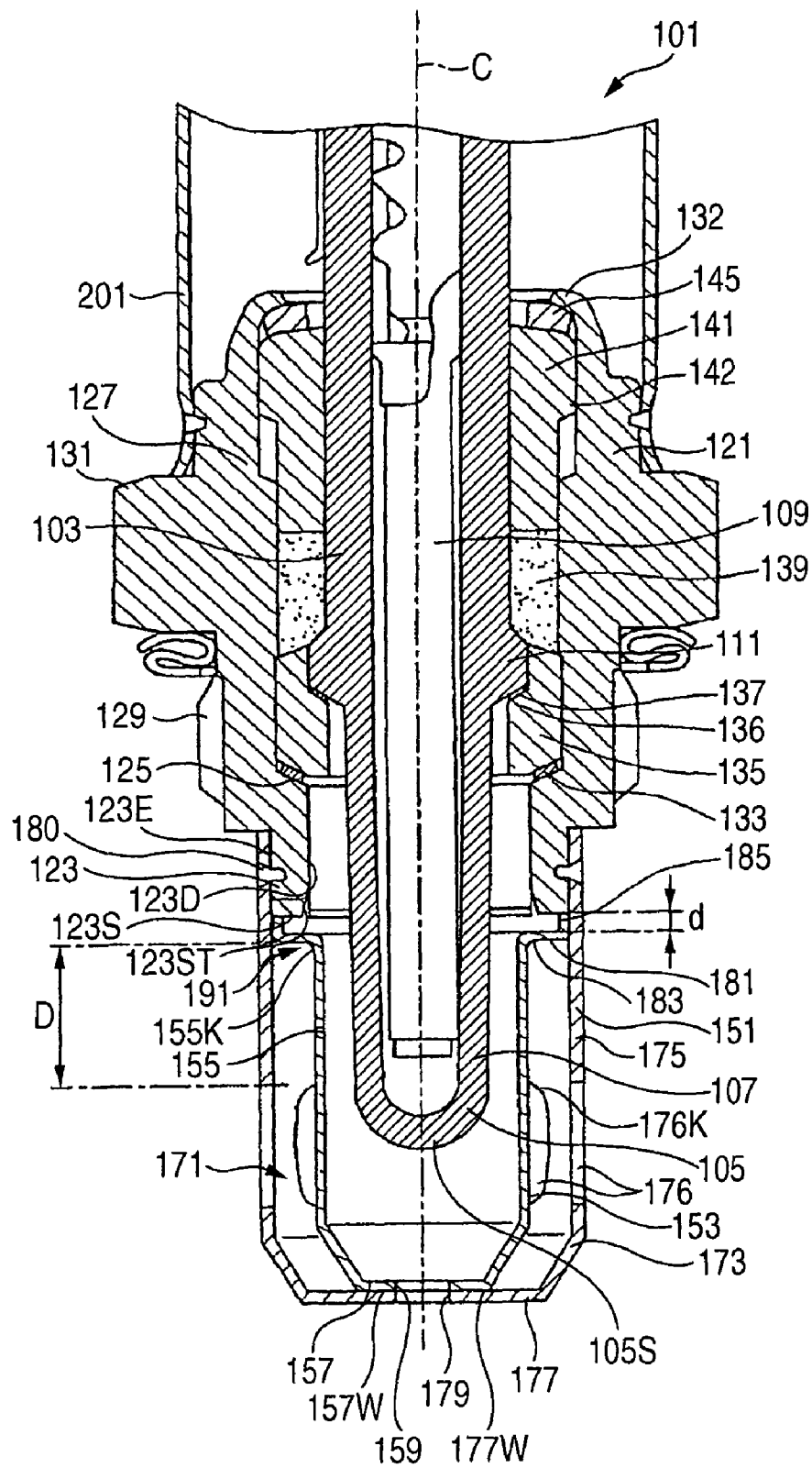
FIG. 3 is a sectional view of an essential portion of the gas sensor according to the embodiment.
Figure 4:
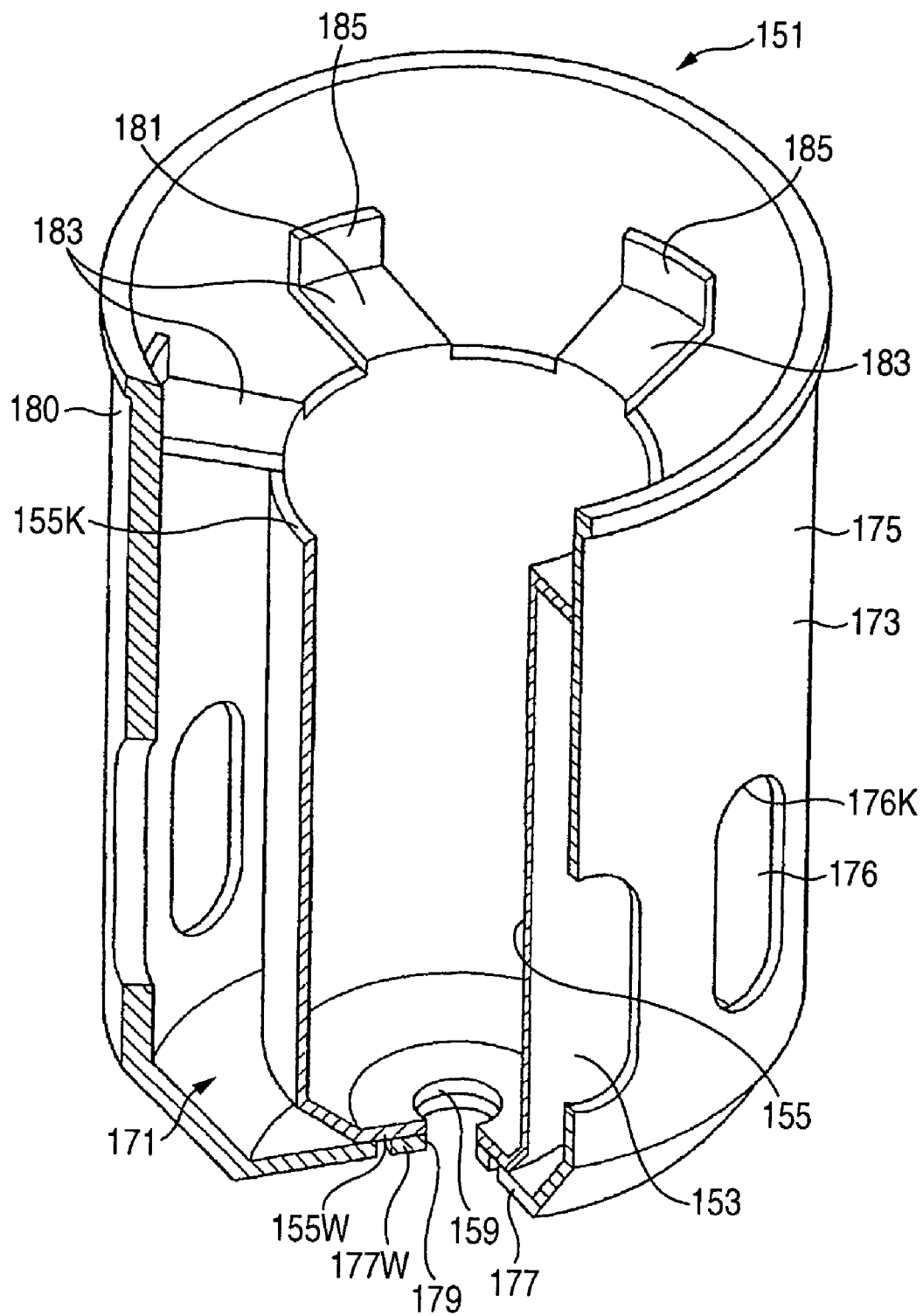
FIG. 4 is an explanatory view showing a protect of the gas sensor according to the embodiment.

A sectional view of a gas sensor 101 according to the embodiment is presented in FIG. 1; a top plan view of an essential portion is presented in FIG. 2, and a sectional view of the essential portion is presented in FIG. 3. Moreover, a protector 151 is shown in FIG. 4. Here in FIG. 1 to FIG. 4, the lower portion shows a leading end side, and the upper portion shows a trailing end side. This gas sensor 101 is an oxygen sensor, which is attached to the exhaust gas pipe of an internal combustion engine for measuring the oxygen concentration in the exhaust gas. The gas sensor 101 is provided with: a gas sensor element 103 extending in the direction of an axis C; a cylindrical metal shell 121 enclosing the gas sensor element 103; and the protector 151 covering such a leading end portion 105 of the gas sensor element 103 as will be exposed to the exhaust gas.

Of these, the gas sensor element 103 has gas sensing characteristics and is provided with a gas detecting portion 107, which is formed into a bottomed cylindrical shape having a closed leading end 105S and can measure the oxygen concentration in an object gas to be measured. In the inner side of this gas detecting portion 107, moreover, there is inserted a rod-shaped heater portion 109 for heating the gas detecting portion 107. The gas sensor element 103 is further provided near the axial center with a bulging portion 111, which bulges radially outward. This bulging portion 111 is utilized for holding the gas sensor element 103 in the metal shell 121.

The metal shell 121 is provided with a relatively thin leading end portion 123, which is inserted into the protector 151. The metal shell 121 is further provided on its inner circumference with a shelf portion (or a support face) 125, which is located at a position on the trailing end side of the leading end portion 123 for holding (or supporting) the gas sensor element 103 in the axial direction. Moreover, a stepped portion 127 is formed on the trailing end side of the shelf portion 125. On the other hand, the metal shell 121 is provided on its outer circumference with a mounting threaded portion 129, which is located on the trailing end side of the leading end portion 123 for mounting the gas sensor 101 in the exhaust gas pipe. Moreover, the mounting threaded portion 129 is provided on its trailing end side with a hexagonal flange portion 131 (or a tool engaging portion), which is utilized when the gas sensor 101 is attached to the exhaust gas pipe.

This metal shell 121 holds the gas sensor element 103 so coaxially that the leading end portion 105 of the gas sensor element 103 protrudes from the leading end face of the metal shell 121. Specifically, a first leaf packing 133 is arranged on the shelf portion 125 of the metal shell 121. On the packing 133, there is further arranged a cylindrical first fixing member 135, which has a stepped portion on its inner circumference. The gas sensor element 103 is inserted through the first fixing member 135 so that its bulging portion 111 comes into engagement with the stepped portion 136 of the first fixing member 135 through a second leaf packing 137. On the trailing end side of the first fixing member 135, there is formed a filled sealing layer 139, which is filled with powder in the clearance defined by the outer circumference of the gas sensor element 103 and the inner circumference of the metal shell 121. On the trailing end side of the filled sealing layer 139, moreover, there is arranged a cylindrical second fixing member 141, which has a stepped portion 142 on its outer circumference and which admits the gas sensor element 103 therethrough on its inner side. On the trailing end side of the second fixing member 141, there is arranged an additionally fastened ring 145, which is additionally fastened by the trailing end portion 132 of the metal shell 121.

The protector 151 is made of a double structure, which has a cylindrical inner cover portion 153 for covering the leading end portion 105 of the gas sensor element 103 through a clearance and a cylindrical outer cover portion 173 arranged around the inner cover portion 153.

Of these, the outer cover portion 173 is made of a metallic material having a thickness of about 0.5 mm and is composed of an outer cylindrical portion 175 (having an external diameter of about 13.1 mm) and an outer bottom portion 177 located on the leading end side of the former. The outer cylindrical portion 175 is provided at its eight portions with outer gas introducing apertures 176, which can introduce the object gas from the outside into the inner side of the outer cover portion 175. The outer gas introducing apertures 176 individually have an elliptical shape and are arranged at an equal spacing in the circumferential direction and at positions on the leading end side from the center, as viewed in the axial direction. The outer bottom portion 177 is provided at its center with an outer leading end air vent hole 179 having a circular shape, which is connected to the outside in the leading end direction of the protector 151.

The inner cover portion 153 is made of a metallic material having a thickness of about 0.3 mm and is composed of an inner cylindrical portion 155 (having an external diameter of about 8.5 mm) and an inner bottom portion 157 located on the leading end side of the former. Unlike the outer cylindrical portion 175, the inner cylindrical portion 155 has no air vent hole. On the other hand, the inner bottom portion 157 is provided at its center with an inner leading end air vent hole 159 having a circular shape, which is connected to the outside in the leading end direction.

On the other hand, the protector 151 is provided with shielding portions 181 for shielding such an inter-cover space 171 circumferentially intermittently on the trailing end side of the outer gas introducing apertures 176 as is defined by the inner cylindrical portion 155 of the inner cover portion 153 and the outer cylindrical portion 175 of the outer cover portion 173. The shielding portions 181 of the embodiment are formed of flange portions 183, which protrude at six portions radially outward from the trailing end 155K of the inner cylindrical portion 155. The area (i.e., the projected area when the shielding portions 181 are projected in the axial direction) of the shielding portions 181 (or the flange portions 183) to the open area of the outer gas introducing apertures 176 is set to about 22%. These flange portions 183 are provided with six leg portions 185, which protrude axially from the radially outer ends of the flange portions 183 to the trailing end side.

In the inner cover portion 153 and the outer cover portion 173, the inner bottom portion 157 and the outer bottom portion 177 are fixed to each other through a clearance of about 0.1 mm by spot-welding them partially at four portions of the surrounding portion 157W of the inner leading end air vent hole 159 and the surrounding portion 177W of the outer leading end air vent hole 179. As a result, the inner leading end air vent hole 159 and the outer leading end air vent hole 179 communicate with each other. Moreover, the inner cylindrical portion 155 and the outer cylindrical portion 175 are so arranged that the side wall of the inner cylindrical portion 155 is located at a position to confront the outer gas introducing apertures 176 and that the inner cylindrical portion 155 and the outer cylindrical portion 175 are parallel to each other.

This protector 151 is so fixed that the trailing end portion 180 of the outer cover portion 173 (i.e., the trailing end portion of the outer cylindrical portion 175) is laser-welded to the outer circumference 123E of the leading end portion 123 of the metal shell 121. Moreover, the leg portions 185 connected to the shielding portions 181 abut against the leading end face 123S of the leading end portion 123 of the metal shell 121.

As a result, the leading end portion 123 of the metal shell 121, the outer cylindrical portion 175 and the inner cylindrical portion 155 construct an inner gas introducing passage 191 for introducing the object gas introduced from the outer gas introducing apertures 176, into the clearance between the inner cover portion 153 and the leading end portion 105 of the gas sensor element 103. Specifically, the inner gas introducing passage 191 guides the object gas introduced from the outer gas introducing apertures 176, between the outer cylindrical portion 175 and the inner cylindrical portion 155 to the trailing end side. After this, the object gas is guided over the trailing end 155K of the inner cylindrical portion 155 closer to the leading end side of the leading end portion 123 of the metal shell 121, as viewed in the axial direction, than the inner circumferential side end edge 123ST of the joining face (or the leading end face) joining an inner circumference 123D and the outer circumference 123E. Then, the object gas is guided into the clearance between the inner cover portion 153 and the leading end portion 105 of the gas sensor element 103 and is discharged through the inner leading end air vent hole 159 and the outer leading end air vent hole 179 to the outside of the protector 151.

As shown in FIG. 1, a leading end portion 201S of a cylindrical metallic outer cylinder 201 is fixed from the outer side to the trailing end side of the hexagonal flange portion 131 of the metal shell 121 by the laser-welding method. Moreover, a grommet 203 made of rubber or the like is fitted and sealed by an additional fastening in a trailing end opening 201K of the metallic outer cylinder 201. At the center of the grommet 203, there is arranged a filter member 205 for introducing the atmosphere into the metallic outer cylinder 201 while preventing the in filtration of moisture. The grommet 203 is provided on its leading end side with a separator 207, which is made of insulating alumina ceramics. Moreover, sensor output lead wires 211 and 212 and heater lead wires 213 and 214 are arranged through the grommet 203 and the separator 207. Still moreover, the connector portions 215B and 215C of first and second sensor terminal fittings 215 and 216 and heater terminal fittings 217 and 218 are held in the separator 207 while being insulated from each other.

In the first sensor terminal fitting 215, the connector portion 215B grips and connects the sensor output lead wire 211 electrically, and the connector portion 215C is inserted into the bottomed hole of the gas detecting portion 107 and electrically connected with the in-sensor electrode layer. In the second sensor terminal fitting 216, moreover, the connector portion 216B grips and connects the sensor output lead wire 212 electrically, and the connector portion 216C grips the outer circumference near the trailing end of the gas detecting portion 107 and is electrically connected with the in-sensor electrode layer. On the other hand, the heater terminal fittings 217 and 218 are electrically connected with the heater lead wires 213 and 214, respectively, and are electrically connected with the electrode pads 109B and 109C of the heater portion 109, respectively.

EXAMPLES

Next, the responsibility and the water resistance were individually investigated on the gas sensor 101 according to the embodiment.

In the gas sensor 101 according to the embodiment, the shortest distance between the leading end portion 123 of the metal shell 121 and the trailing end 155K of the inner cylindrical portion 155 (i.e., the distance between the inner circumferential side end edge 123ST of the leading end portion 123 of the metal shell 121 and the trailing end 155K of the inner cylindrical portion 155 in this embodiment) was designated by d. Moreover, the shortest distance in the axial direction between the trailing end 155K of the inner cylindrical portion 155 and the trailing side ends 176K of the outer gas introducing apertures 176 was designated by D. For the investigation, moreover, under the condition of d+D=5.9 (mm): the gas sensor having the value of d/D of about 0.010 was used as Example 1; the gas sensor having the value of d/D of about 0.079 was used as Example 2; the gas sensor having the value of d/D of about 0.105 was used as Example 3; the gas sensor having the value of d/D of about 0.150 was used as Example 4; the gas sensor having the value of d/D of about 0.200 was used as Example 5; and the gas sensor having the value of d/D of about 0.217 was used as Example 6.

The investigation was performed by attaching a test oxygen sensor to the exhaust pipe of a straight 4-cylinder gasoline engine having a displacement of 2,000 cc and an injector and by measuring the output values of the oxygen sensor. The gasoline engine was driven at a speed of 2,000 rpm (revolutions/minute) with lead-free gasoline. The exhaust temperature was about 450° C. In this measurement, the switching control was forcibly made at 0.5 Hz between a rich condition (i.e., $\lambda$=0.97) and a lean condition (i.e., $\lambda$=1.03) by a controlling oxygen sensor, when the stoichiometric value of the air/fuel (i.e., air/gasoline) ratio of 14.7 was $\lambda$=1. Moreover, there were added the time period Trs for which the output of the test oxygen sensor varied to a value corresponding to $\lambda$=1 after the condition had been changed from rich to lean, and the time period Tls for which the output of the test oxygen sensor varied to the value corresponding to $\lambda$=1 after the condition had been changed from lean to rich. The results are enumerated in Table 1. The results of the responsibility test are presented with the ratios when the response time of Example 1 was set at 1.

In the water resistance test, moreover, the gas sensor 101 was so attached as to protrude into the exhaust pipe having an internal diameter of 50 mm. In this exhaust pipe, water was injected under a pressure of 0.2 MPa from the nozzle into the gas sensor 101, the air was blown at a velocity of 3 m/s for 5 seconds and stopped for 5 seconds. This cycle was repeated three times. Just after this, the appearance of the gas sensor element 103 in the protector 151 was observed to confirm the presence of water droplets. As a result, the gas sensor element 103 was judged to be good, if it had water droplets, but no good if it had no water droplet. The investigation was performed on ten samples for each test.

On the other hand, the synthetic decision was made by judging the responsibility and the water resistance synthetically, and both good results are indicated by ○ whereas one not so good results are indicated by △.

TABLE 1

|  | d/D | A | B | C |
| --- | --- | --- | --- | --- |
| Ex. 1 | 0.010 | 1 | 0 | △ |
| Ex. 2 | 0.079 | 0.948 | 0 | ○ |
| Ex. 3 | 0.105 | 0.952 | 0 | ○ |
| Ex. 4 | 0.150 | 0.947 | 0 | ○ |
| Ex. 5 | 0.200 | 0.953 | 0 | ○ |
| Ex. 6 | 0.217 | 0.955 | 6 | △ |

A: Ratio to 1 of Response Time of Comparison 1
B: Results (NG Number) of Water Resistance
C: Synthetic Decision On the responsibility tests, as apparent from Table 1, Example 2 to Example 6 are better by about 0.05 (i.e., 5%) at the ratio of the response time than Example 1. Therefore, it is found that the gas sensors of Example 2 to Example 6 are superior in responsibility to that of Example 1. These results are thought to come from that the resistance to occur in the inner gas introducing passage 191 is not reduced to exert influences on the response unless the value d/D takes a considerable value, that is, unless the distance d is rather larger than the distance D. It is also found that the improvement of the response is hardly influenced if the distance d is far larger than the distance D. Considering the responsibility of the sensor, it is advisable that the ratio of d/D is 0.075 or more.

On the other hand, the water resistance tests confirmed that Example 1 to Example 5 were excellent in the water resistance but that the water resistance was poor in Example 6. It is, therefore, found that the gas sensors of Example 1 to Example 5 were excellent in water resistance. It is thought that the condensed water having infiltrated from the outer gas introducing apertures 176 will pass the inner gas introducing passage 191 and flow into the inner cover portion 155, if the ratio d/D takes an excessively large value, that is, if the distance d becomes far smaller than the distance D. From these results, it is thought that the water resistance can be especially improved if the gas sensor is designed to have the ratio d/D of 0.200 or less.

Judging those responsibility tests and water resistance tests synthetically, moreover, it can be said that Example 1 is inferior in the responsibility and that Example 6 is inferior in the water resistance, but that Example 2 to Example 6 are superior both in the responsibility and the water resistance.

As has been described hereinbefore, the gas sensor 101 of the embodiment is provided with the outer gas introducing apertures 176 in the outer cylindrical portion 175 of the outer cover portion 173. Moreover, the gas sensor 101 is provided with the inner gas introducing passage 191, which is defined by the leading end portion 123 of the metal shell 121, the outer cylindrical portion 175 of the outer cover portion 173 and the inner cylindrical portion of the inner cover portion 153. Still moreover, the gas sensor 101 is provided with the inner leading end through hole 159 formed in the leading end direction of the inner cover portion 153 and the outer leading end through hole 179 formed in the leading end direction of the outer cover portion 173.

Therefore, the object gas having intruded from the outside through the outer gas introducing apertures 176 into the inside flows between the outer cover portion 173 and the inner cover portion 153 to the trailing end side and further flows via the inner gas introducing passage 191 into the inside of the inner cover portion 153. After this, the object gas flows to the leading end side in the clearance between the inner cover portion 153 and the leading end portion 105 of the gas sensor element 103. After this, the object gas is discharged to the outside through the inner leading end through hole 159 and the outer leading end through hole 179. Therefore, the object gas has excellent inflow characteristics. In case the gas sensor 101 is used with its leading end being directed downward, on the other hand, the condensed water having intruded together with the object gas from the outside into the inside through the outer gas introducing apertures 176 flows along the outer wall face of the inner cylindrical portion of the inner cover portion 153 to the leading end side. As a result, the condensed water hardly wets and breaks the gas sensor element 103. Therefore, this gas sensor 101 is excellent not only in the responsibility as the sensor but also in the water resistance.

Especially in this gas sensor 101, the inner gas introducing passage 191 is formed closer to the leading end side than the existing gas sensor disclosed in JP-A-2002-162377, so that the distance from the inner gas introducing passage 191 to the leading end portion 105 of the gas sensor element 103 can be shortened to improve the responsibility of the sensor. Moreover, the inner gas introducing passage 191 is disposed on the leading end side so that the gas sensor 101 can be diametrically reduced without being influenced by the size of the inner circumference 123D of the leading end portion 123 of the metal shell 121.

In addition, this gas sensor 101 has the double structure in the protector 151 so that it can reduce the number of parts and the number of manufacturing steps. Thus, the gas sensor 101 can be manufactured at a reasonable cost.

In this embodiment, moreover, the side wall of the inner cylindrical portion 155 exists at the position confronting the outer gas introducing apertures 176, and the inner cylindrical portion 155 and the outer cylindrical portion 175 are parallel to each other. Therefore, the object gas introduced from the outer gas introducing apertures 176 easily flows along the outer wall face of the inner cylindrical portion 175 to the trailing end side so that it can be quickly fed at a high rate to the inner gas introducing passage 191.

Moreover, the aforementioned value d/D is set to 0.075 or more and 0.200 or less so that the water resistance of the gas sensor element 103 can be improved while realizing the quick responsibility.

Moreover, the embodiment is provided with the shielding portions 181 so that the condensed water having intruded together with the object gas can be more effectively prevented from intruding into the inside via the inner gas introducing passage 191 while keeping the fluidity of the object gas introduced from the outer gas introducing apertures 176. Therefore, it is possible to improve the water resistance of the gas sensor 101 better.

In this embodiment, moreover, the ratio of the area of the shielding portions 181 to the open area of the outer gas introducing apertures 176 is set to about 22% in the range from 5% to 40%. Therefore, the effect of preventing the intrusion of the condensed water can be sufficiently retained together with the fluidity of the object gas.

In the embodiment, moreover, the outer leading end air vent hole 179 and the inner leading end air vent hole 159 communicate with each other through the clearance of about 0.1 mm. As a result, little object gas flows through the clearance between the outer bottom portion 177 and the inner bottom portion 157 so that the object gas in the inner cover portion 153 can be efficiently discharged to the outside by the Venturi effect of the object gas flowing outside.

In the embodiment, moreover, the surrounding portion 177W of the outer leading end air vent hole 179 and the surrounding portion 157W of the inner leading end air vent hole 159 are fixedly spot-welded so that the outer cover portion 173 and the inner cover portion 153 can be reliably prevented from relatively going out of position.

The invention has been described in connection with its embodiment but should not be limited to the embodiment or the like thus far described. It goes without saying that the invention can be suitably modified without departing from the gist thereof.

For example, the embodiment has exemplified the outer cover portion 173, which has the outer leading end air vent hole 179 in the leading end side of the outer cylindrical portion 175. However, the outer cover portion can have a bottomed outer bottom portion having no air vent hole in the leading end side of the outer cylindrical portion. Alternatively, the inner cover portion can protrude more to the leading end side than the outer cover portion, and the outer cylindrical portion can be provided on the leading end side of the outer cylindrical portion with an inner cover approaching portion, which comes close to or abuts against the inner cover portion.

Moreover, the embodiment has exemplified the inner cover portion 153, which is located on the leading end side of the inner cylindrical portion 155 and has the inner leading end air vent hole 159 communicating with the outside closer in the leading end direction than the protector 151. However, the inner cover portion can be modified such that the inner leading end air vent hole formed in the leading end side of the inner cylindrical portion is arranged to communicate with the space in the outer cover portion.

Moreover, the embodiment has exemplified the gas sensor 101 having the inner cylindrical portion 153 and the outer cylindrical portion 173 in parallel. However, the gas sensor can be modified such that the inner cylindrical portion and the outer cylindrical portion have the smaller spacing toward the leading end side.

Moreover, the embodiment has exemplified the gas sensor 101 having the outer leading end air vent hole 179 and the inner leading end air vent hole 159 connected to each other through the clearance. However, the gas sensor can be modified such that the outer cover portion and the inner cover portion contact closely with each other to connect the outer leading end air vent hole and the inner leading end air vent hole.

Moreover, the embodiment has exemplified the gas sensor element 103 having the bottomed cylindrical shape. However, the gas sensor element can have a plate shape.

In the embodiment, moreover, the outer gas introducing apertures 176 have the elliptical shape, and the inner leading end air vent hole 159 and the outer leading end air vent hole 179 have the circular shape. However, the shapes of those holes can be suitably modified into an elliptical or rectangular shape.

In the embodiment, moreover, the shielding portions 181 protrude radially outward at the six portions. However, the number and shape of the shielding portions should not be limited there to but can be suitably modified.

This application is based on Japanese Patent application JP 2003-187822, filed Jun. 30, 2003, the entire content of which is hereby incorporated by reference, the same as if set forth at length.

What is claimed is:

1. A gas sensor comprising:
   a gas sensor element extending in an axial direction and having gas sensing characteristics at least at its own leading end portion;
   a cylindrical metal shell enclosing said gas sensor element such that said leading end portion of said gas sensor element protrudes from its own leading end, and including a support face formed on its inner circumference for supporting an axial direction of said gas sensor element; and
   a protector fixed on said metal shell and covering said leading end portion of said gas sensor element,
   wherein said protector has a double structure including a cylindrical inner cover portion covering said leading end portion of said gas sensor element through a clearance and a cylindrical outer cover portion arranged around said inner cover portion,
   said outer cover portion includes an outer cylindrical portion having outer gas introducing apertures capable of introducing an object gas to be measured from an outside into an inside of said outer cover portion,
   said inner cover portion includes:
   an inner cylindrical portion enclosing said leading end portion of said gas sensor element; and
   an inner leading end air vent hole positioned on a leading end side of said inner cylindrical portion, and
   a leading end portion positioned on a leading end side of said support face of said metal shell, said outer cylindrical portion and said inner cylindrical portion are arranged to construct an inner gas introducing passage for guiding said object gas introduced from said outer gas introducing apertures, between said outer cylindrical portion and said inner cylindrical portion, across an edge of said inner cylindrical portion disposed at a trailing end of said inner cylindrical portion farthest from a leading end of the inner cylindrical portion in an axial direction into a clearance formed between said inner cover portion and said leading end portion of said gas sensor element,
   wherein when a shortest distance between said leading end portion of said metal shell and a trailing end of said inner cylindrical portion is designated by d and when a shortest distance in an axial direction between a trailing end of said inner cylindrical portion and a trailing side end of said outer gas introducing apertures is designated by D, a ratio d/D is within a range from 0.075 to 0.200,
   wherein an outer circumferential surface of the inner cylindrical portion is not provided with an air vent hole.

2. The gas sensor according to claim 1, wherein the ratio d/D is within a range from 0.080 to 0.180.

3. The gas sensor according to claim 1, wherein the ratio d/D is within a range from 0.100 to 0.150.

4. The gas sensor according to claim 1, wherein, of an inter-cover space between said inner cylindrical portion of said inner cover portion and said outer cylindrical portion of said outer cover portion, shielding portions are provided closer to a trailing end side than said outer gas introducing apertures for shielding said inter-cover space intermittently in a circumferential direction.

5. The gas sensor according to claim 4, wherein a ratio of an area of said shielding portions to an open area of said outer gas introducing apertures is set within a range from 5% to 40%.

6. The gas sensor according to claim 1,
   wherein said outer cover portion includes an outer bottom portion positioned on a leading end side of said outer cylindrical portion and having an outer leading end air vent hole,
   said inner cover portion includes an inner bottom portion positioned on a leading end side of said inner cylindrical portion and having said inner leading end air vent hole,
   said outer bottom portion and said inner bottom portion either contacts closely with each other or is positioned close to each other through a clearance of 0.2 mm or less at least between a surrounding portion of said outer leading end air vent hole and a surrounding portion of said inner leading end air vent hole, and
   said outer leading end air vent hole and said inner leading end air vent hole communicate with each other.

7. The gas sensor according to claim 6, wherein a surrounding portion of said outer leading end air vent hole of said outer cover portion and a surrounding portion of said inner leading end air vent hole of said inner cover portion are fixed to each other.

8. The gas sensor according to claim 1, wherein
   said inner cylindrical portion and said outer cylindrical portion are arranged such that a side wall of said inner cylindrical portion is disposed at a position to confront said outer gas introducing apertures and such that said inner cylindrical portion and said outer cylindrical portion are either parallel to each other or closer to each other as they go farther to a leading end side.

9. The gas sensor according to claim 1, wherein an annular clearance is formed between the cylindrical inner cover portion and the cylindrical outer cover portion.

* * * * *